United States Patent
Lutkenhaus et al.

(10) Patent No.: US 12,097,112 B2
(45) Date of Patent: Sep. 24, 2024

(54) OPHTHALMIC LENSES FOR BALANCING COMA ABERRATIONS

(71) Applicant: Alcon Inc., Fribourg (CH)

(72) Inventors: Jeffrey Ryan Lutkenhaus, Fort Worth, TX (US); Shinwook Lee, Arlington, TX (US); Sangyeol Lee, North Richland Hills, TX (US); Daniel Robert Carson, Fort Worth, TX (US); Zaiwei Xu, Fort Worth, TX (US)

(73) Assignee: Alcon Inc., Fribourg (CH)

( * ) Notice: Subject to any disclaimer, the term of this patent is extended or adjusted under 35 U.S.C. 154(b) by 197 days.

(21) Appl. No.: 17/804,120

(22) Filed: May 26, 2022

(65) Prior Publication Data

US 2022/0401212 A1 Dec. 22, 2022

Related U.S. Application Data

(60) Provisional application No. 63/211,344, filed on Jun. 16, 2021.

(51) Int. Cl.
*A61F 2/16* (2006.01)

(52) U.S. Cl.
CPC ............ *A61F 2/164* (2015.04); *A61F 2/1618* (2013.01)

(58) Field of Classification Search
CPC ..................................................... A61F 2/164
See application file for complete search history.

(56) References Cited

U.S. PATENT DOCUMENTS

| | | | |
|---|---|---|---|
| 8,647,383 B2 | 2/2014 | Sanger et al. | |
| 8,858,627 B1* | 10/2014 | Lindstrom | A61F 2/1648 623/6.37 |
| 9,265,603 B2 | 2/2016 | Sanger et al. | |
| 2004/0106992 A1* | 6/2004 | Lang | A61F 2/1618 623/901 |
| 2005/0187622 A1 | 8/2005 | Sandstedt et al. | |
| 2009/0062911 A1 | 3/2009 | Bogaert | |
| 2010/0057202 A1* | 3/2010 | Bogaert | A61F 2/1613 623/6.27 |
| 2017/0245983 A1* | 8/2017 | Hong | A61F 2/164 |

FOREIGN PATENT DOCUMENTS

WO 2020236330 A1 11/2020

\* cited by examiner

*Primary Examiner* — Javier G Blanco
(74) *Attorney, Agent, or Firm* — PATTERSON + SHERIDAN, LLP

(57) ABSTRACT

The present disclosure provides an ophthalmic lens that is disposed to balance coma aberrations if the lens, when inserted in a patient's eye, is decentered or tilted with respect to an optical axis of the patient's eye, and maintain a substantially diffraction-limited image quality if the lens, when inserted in the patient's eye, is centered with respect to the optical axis of the patient's eye. The lens may include an optic having an anterior surface and an opposing posterior surface disposed about an optical axis of the lens. One of the surfaces (e.g., the anterior surface) may have a semi-aspheric surface profile, which includes an inner region having a substantially spherical surface profile and extending radially from the optical axis of the lens to a first boundary, and an outer region having an aspherical surface profile and extending radially at least beyond the first boundary to a second boundary.

21 Claims, 5 Drawing Sheets

OPHTHALMIC LENSES FOR BALANCING COMA ABERRATIONS

PRIORITY CLAIM

This application claims the benefit of priority of U.S. Provisional Patent Application Ser. No. 63/211,344 titled "OPHTHALMIC LENSES FOR BALANCING COMA ABERRATIONS," filed on Jun. 16, 2021, whose inventors are Jeffrey Ryan Lutkenhaus, Shinwook Lee, Sangyeol Lee, Daniel Robert Carson and Zaiwei Xu, which is hereby incorporated by reference in its entirety as though fully and completely set forth herein.

FIELD

The present disclosure generally relates to the field of ophthalmic lenses, and more specifically to lenses that are disposed to balance coma aberrations.

BACKGROUND

Ophthalmic lenses, such as intraocular lenses (IOLs), are routinely implanted in patients' eyes during cataract surgery to replace the natural crystalline lenses. The optical power of the natural crystalline lens can vary under the influence of the ciliary muscles to provide accommodation for viewing objects at different distances from the eye. Many IOLs incorporate aspherical surfaces to counter the positive spherical aberration of the cornea. However, aspherical IOLs are more sensitive to tilt and decentration, resulting in coma aberrations and a reduction in image quality.

SUMMARY

The present disclosure is generally directed to an ophthalmic lens (such as an IOL) that is disposed to balance coma aberrations if the lens, when inserted in a patient's eye, is decentered or tilted with respect to an optical axis of the patient's eye, and maintain a substantially diffraction-limited image quality if the lens is centered with respect to the optical axis of the patient's eye.

In accordance with the present disclosure, the lens may include an optic having an anterior surface and an opposing posterior surface disposed about an optical axis of the lens. One of the anterior and posterior surfaces may have an aspherical surface profile, and the other of the surfaces may have a semi-aspherical surface profile. The semi-aspherical surface profile may include an inner region having a substantially spherical surface profile and extending radially from the optical axis of the optic to a first boundary, and an outer region having an aspherical surface profile and extending radially from or beyond the first boundary to a second boundary.

The semi-aspherical surface profile may be defined by the equation:

$$z(x) = \frac{cx^2}{1+\sqrt{1-c^2x^2}} + a_4 x^4 + a_6 x^6 + a_8 x^8 \text{ where } 0 < x < R,$$

wherein
x denotes a radial distance from the optical axis of the optic,
c denotes a base curvature of the surface,
R denotes a total radial distance from the optical axis of the optic to the second boundary,
$a_4$ is a fourth order aspheric coefficient,
$a_6$ is a sixth order aspheric coefficient, and
$a_8$ is an eighth order aspheric coefficient.

As understood by one of ordinary skill in the art, the drawings described below are for illustration purposes only, and are not intended to limit the scope of the present disclosure.

DETAILED DESCRIPTION

Spherical aberration in the human eye is a combination of the positive spherical aberration of the cornea and the negative spherical aberration of the crystalline lens in the eye. In healthy eyes, the positive spherical aberration of the cornea is compensated by the negative spherical aberration of the lens; as a result, the overall spherical aberration is low. However, as the eyes age, the optical properties of the crystalline lenses change, resulting in an overall positive spherical aberration and decreased optical performance.

Monofocal IOLs generally utilize aspherical surfaces to counter the positive spherical aberration of the cornea. Although the image quality in these aspherical lenses may be enhanced to diffraction-limited image quality (as compared to monofocal IOLs with spherical surfaces), the aspheric IOLs are more sensitive to tilt and decentration. Tilt and decentration occur when an implanted IOL is misaligned with respect to the optical axis of the eye. The result of this misalignment is an increase in coma aberration and a reduction in image quality. Coma aberration commonly occurs due to imperfections or misalignments in the lens that results in off-axis point sources appearing distorted, often appearing like a tail ("coma") of a comet. Conventional monofocal IOLs having aspheric surfaces either fail to correct for coma aberration altogether, or are designed to minimize coma aberration when the lens is decentered with respect to the optical axis of the eye, but sacrifice image quality when the lens is aligned with respect to the optical axis of the eye.

The present disclosure is generally directed to an ophthalmic lens (such as an IOL) having a surface profile that is disposed to maintain a near diffraction-limited image quality when the lens is centered with respect to the optical axis of the eye and balance coma aberrations when the lens is decentered with respect to the optical axis of the eye. Although the following disclosure is described in conjunction with IOLs, it is to be understood that the features and elements of the present disclosure are not to be limited to any particular type of IOL and may be applied to monofocal IOLs, monofocal IOLs with an extended depth of focus, multifocal IOLs, or any other type of IOL. Additionally, the present disclosure may further be applied to non-IOL ophthalmic lenses, such as contact lenses. Moreover, as used herein, the term "intraocular lenses" (and its abbreviation IOL) is used to describe lenses that are implanted into the interior of the eye to either replace the eye's natural lens or to otherwise augment vision regardless of whether the natural lens is removed.

Figure 1A:
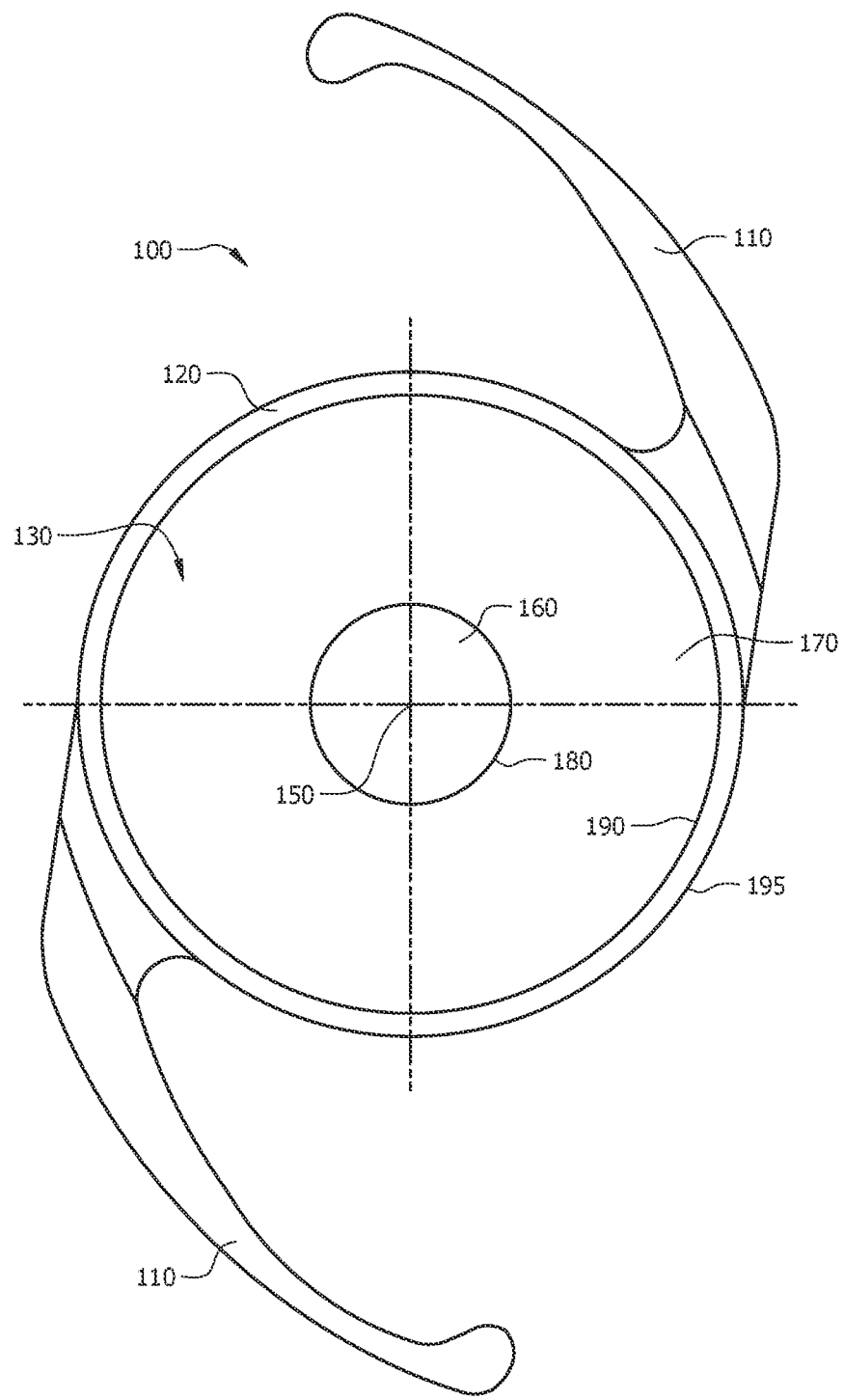
FIG. 1A illustrates a plan view of an example embodiment of an ophthalmic lens, in accordance with the present disclosure.
Figure 1B:
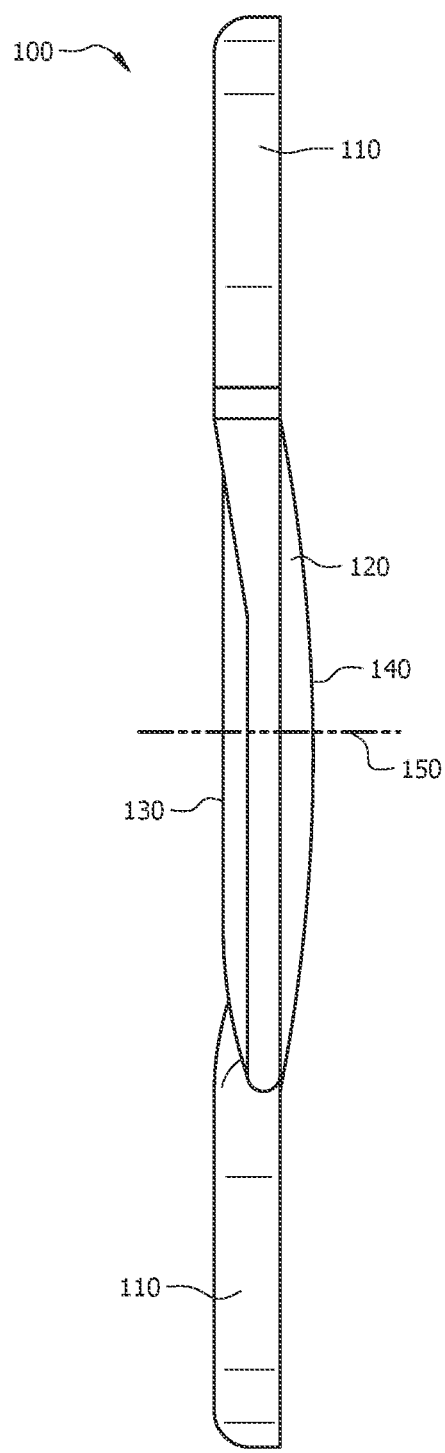
FIG. 1B illustrates a side view of an example embodiment of an ophthalmic lens, in accordance with the present disclosure.

Reference is now made to FIGS. 1A and 1B, wherein are depicted an example embodiment of an intraocular lens 100 according to the present disclosure. FIG. 1A depicts a plan view of an anterior side of the lens 100, and FIG. 1B depicts a side view showing the anterior and the posterior sides of the lens 100. Lens 100 may comprise a plurality of haptics 110 generally operable to position and stabilize the lens 100 within the capsular bag of a patient's eye. Lens 100 may further comprise an optic 120 having an anterior surface 130 and a posterior surface 140 that are disposed about an optical axis 150 of the lens. One of the anterior 130 and posterior 140 surfaces may comprise an aspherical surface profile, and the other of the surfaces may comprise a semi-aspherical surface profile. In FIG. 1A, the semi-aspherical surface profile is depicted on the anterior surface 130 of the optic 120. However, it is to be understood that the semi-aspherical surface profile shown and described in conjunction with FIG. 1A may alternatively be applied on the posterior surface 140 of the optic 120, and the aspheric surface profile may be applied on the anterior surface 130 of the optic 120.

In an embodiment and for purposes of illustration, the present disclosure will describe the aspherical surface profile applied to the posterior surface 140 of the optic 120 (i.e., the surface not shown in FIG. 1A), and the semi-aspherical surface profile applied to the anterior surface 130 of the optic 120.

With continued reference to FIG. 1A, the semi-aspherical surface profile may include an inner region 160 and an outer region 170. The inner region 160 may comprise a substantially spherical surface profile and may extend radially from the optical axis 150 to a first boundary 180. The outer region 170 may comprise a substantially aspherical surface profile and may extend radially from or beyond the first boundary 180 to a second boundary 190. In an embodiment, the second boundary 190 may be formed between the first boundary 180 and the radially outermost edge 195 of the optic 120. In another embodiment, the second boundary 190 may comprise or be congruent to the radially outermost edge 195 of the optic 120.

With continued reference to FIG. 1A, the semi-aspherical surface profile of the anterior surface 130—having the inner region 160 which is substantially spherical and the outer region 170 which is substantially aspherical—is disposed to provide near diffraction-limited image quality if the lens 100, when inserted or implanted in the patient's eye, is centered with respect to the optical axis of the eye, and is disposed to balance coma aberration and provide higher image quality if the lens 100, when inserted or implanted, is decentered or tilted with respect to the optical axis of the eye. "Balancing" a coma aberration refers to a trade-off, e.g., the ability of the lens 100 to improve image quality by reducing coma effects when the lens 100 is decentered or tilted without substantially sacrificing image quality if the lens 100 is centered with respect to the optical axis 150 of the eye. In accordance with the present disclosure, the lens 100 may configured to achieve the described result for patients of various pupil sizes (e.g., 2 mm, 3 mm, 4 mm, 4.5 mm, as further described below.

The composite semi-aspherical surface profile of the anterior surface 130 of the optic 120 shown in FIG. 1A may be defined by the following equation:

$$z(x) = \frac{cx^2}{1 + \sqrt{1-c^2x^2}} + a_4 x^4 + a_6 x^6 + a_8 x^8, \text{ where } 0 < x < R, \quad \text{Eq. (1)}$$

wherein, x denotes a radial distance from the optical axis 150 of the optic 120, c denotes a base curvature of the anterior surface 130 of the optic 120, R denotes a total radial distance from the optical axis 150 of the optic to the second boundary 190 of the optic 120, $a_4$ is a fourth order aspheric coefficient, $a_6$ is a sixth order aspheric coefficient, and $a_8$ is an eighth order aspheric coefficient.

In Eq. (1), the terms $a_4 x^4$, $a_6 x^6$, and $a_8 x^8$ are aspheric terms, wherein aspheric coefficients $a_4$, $a_6$, and as determine the asphericity of the surface profile of the anterior surface 130. The aspheric terms of Eq. (1) are high-order terms that are designed to compensate for coma aberrations caused by decentration and/or tilt of the lens 100. Specifically, these high-order aspheric terms are effective in balancing coma because they allow for the relocation of the focus points (which have been moved off of the retina due to decentration) back to the retina. Eq. (1) excludes low-order aspheric terms (such as $a_2$ and/or $a_3$ terms), as they are redundant with respect to the power of the base curvature, adversely impact rotational symmetry of the lens, and/or are otherwise ineffective in balancing coma. As the radial distance (x) from the optical axis 150 of the lens increases, the surface profile of the anterior surface increases in asphericity. Similarly, when the radial distance (x) from the optical axis 150 of the lens decreases, the surface profile decreases in asphericity. As a result, the inner region 160 (having a comparatively smaller radius than the outer region 170) may be substantially spherical.

With continued reference to Eq. (1), in some embodiments, the base curvature c of the anterior surface 130 may be in the range of about 15 mm to about 25 mm; $a_4$ may be in the range of about $-9.6550 \times 10^{-4}$ mm$^{-3}$ to about $-3.1286 \times 10^{-4}$ mm$^{-3}$; $a_6$ may be in the range of about $-1.4229 \times 10^{-4}$ mm$^{-5}$ to about $2.3848 \times 10^{-4}$ mm$^{-5}$; as may be in the range of about $-1.9439 \times^{-4}$ mm$^{-7}$ to about $2.0641 \times 10^{-4}$ mm$^{-7}$; and R may be in the range of about 0 mm to about 3 mm.

Figure 2A:
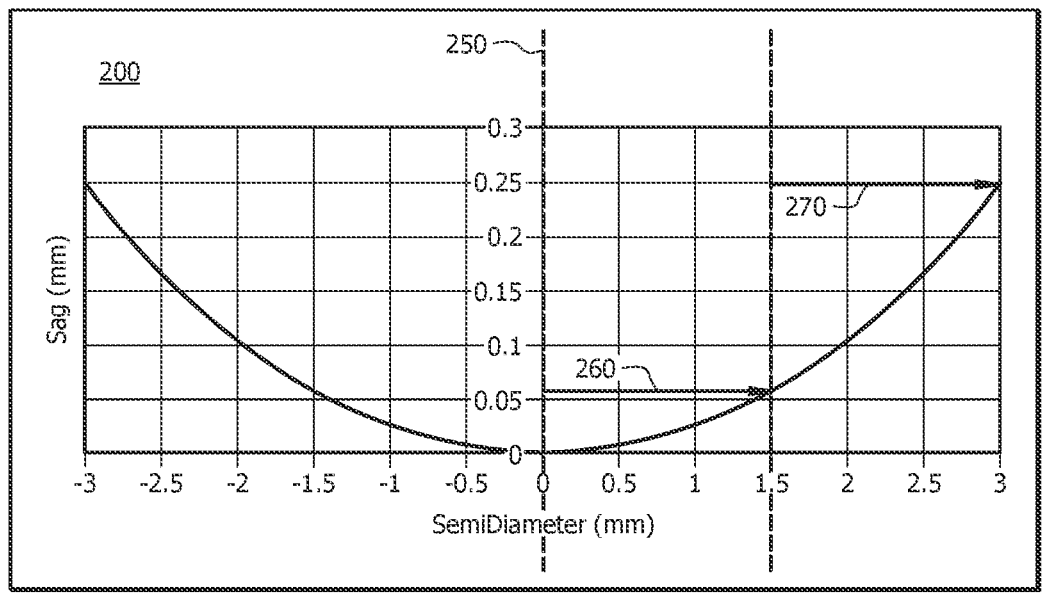
FIG. 2A illustrates a plot of the surface sag versus radial distance from the optical axis for an example optic, in accordance with the present disclosure.

Reference is now made to FIG. 2A, wherein is shown the composite surface profile of a semi-aspherical anterior surface 130 of the optic 120 shown in FIG. 1A and defined by Eq. (1), graphically represented as a plot 200 of sag versus radial distance from the optical axis 250 of the lens. In the plot of FIG. 2A, the radius is zero at the optical axis 250. The sag profile of the inner region 260 of the optic, defined from a radius of 0 mm to 1.5 mm, is substantially spherical. The sag profile of the outer region 270 of the optic, defined from a radius of 1.5 mm to 3 mm, is substantially aspheric and increases in asphericity as the radius increases to the outermost edge of the optic (shown at 3 mm).

Figure 2B:
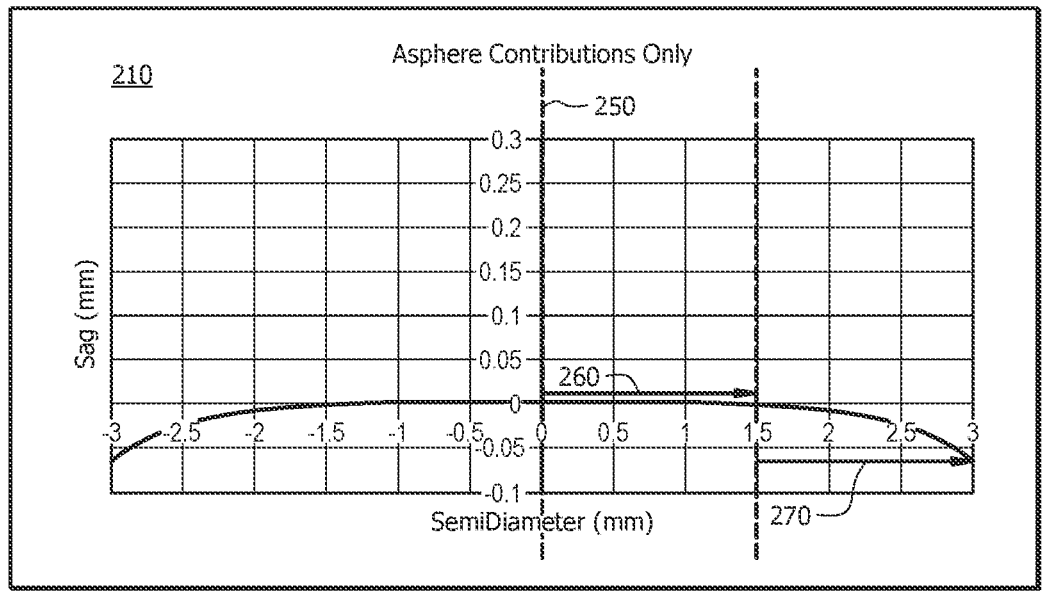
FIG. 2B illustrates a plot of the aspheric contributions of the surface sag versus radial distance from the optical axis for an example optic, in accordance with the present disclosure.

Reference is now made to FIG. 2B, wherein is shown the aspheric contributions of the semi-aspherical anterior surface 130 of the optic 120 shown in FIG. 1A and defined by Eq. (1), graphically represented as a plot 210 of sag versus radial distance from the optical axis 210 of the lens. As shown in FIG. 2B, the aspheric sag measurement in the inner region 260 of the optic (corresponding to a radial distance from 0 mm to 1.5 mm) remains constant at 0 mm, indicating substantially zero asphericity, i.e., a substantially spherical profile in the inner region 260. The aspheric sag measurement in the outer region 270 of the optic (corresponding to a radial distance from 1.5 mm to 3 mm) gradually increases from zero to approximately 0.065 mm, indicating that as the radial distance increases in the outer region 270, the asphericity also increases in the outer region 270. The sag curve of the aspheric contributions bends downward because, as the radius increases beyond the substantially spherical inner region (see element 160 in FIG. 1A), the aspheric contributions of the surface profile increase, thereby bending the curvature away from the spherical center. It is to be understood that, although the inner 260 and outer 270 regions are delineated by their radial measurements on the positive side of the x-axis in FIGS. 2A and 2B, these regions are three-dimensional regions extending to both sides of the x-axis.

Figure 3A:
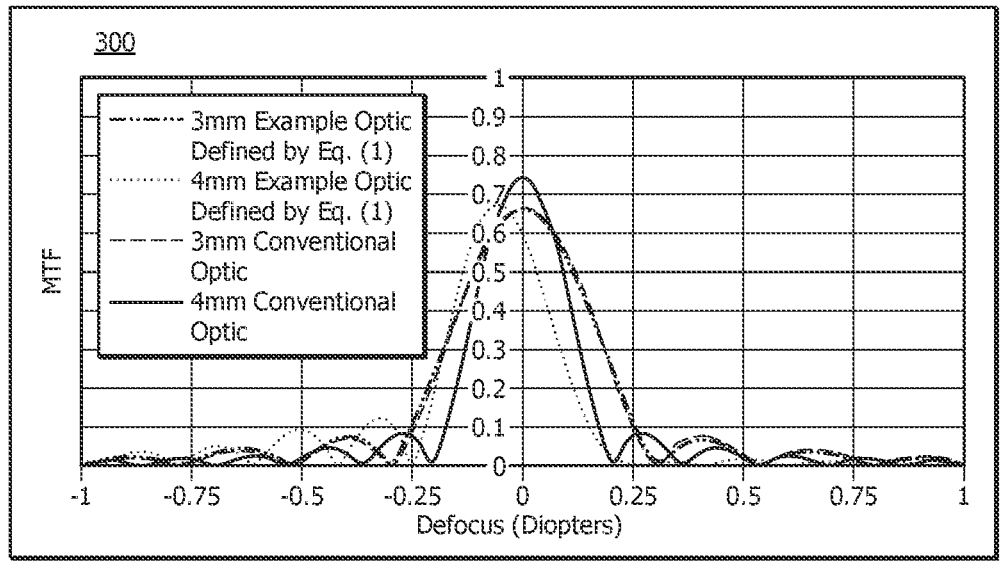
FIG. 3A illustrates comparative through-focus modulation transfer function (MTF) plots for example optics and conventional optics for different pupil sizes, wherein the optics are centered with respect to the optical axis of the eye, in accordance with the present disclosure.
Figure 3B:
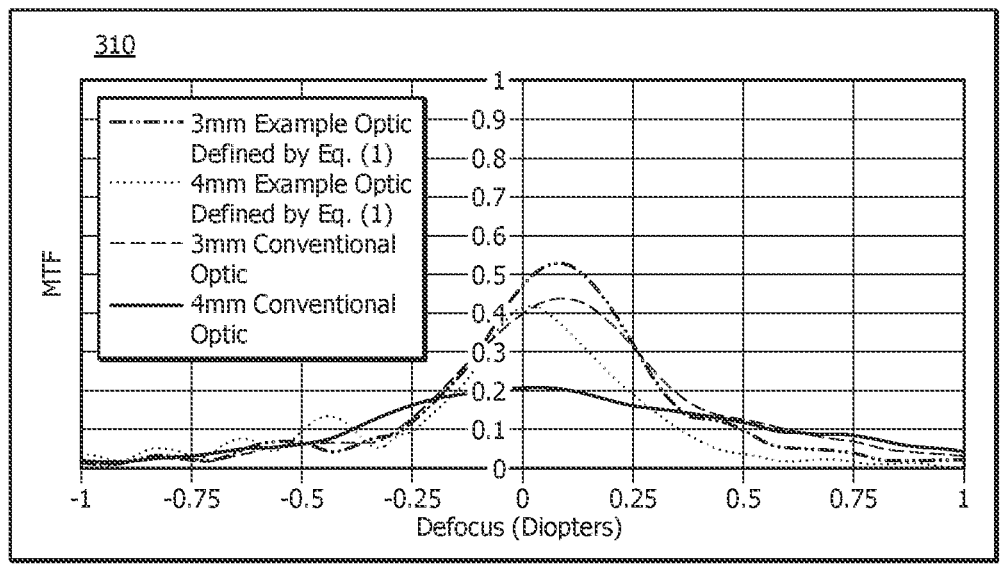
FIG. 3B illustrates comparative through-focus MTF plots for example optics and conventional optics for different pupil sizes, wherein the optics are decentered with respect to the optical axis of the eye, in accordance with the present disclosure.

Reference is now made to FIGS. 3A and 3B, wherein are shown comparative through-focus modulation transfer function (MTF) plots for different pupil sizes (3 mm and 4 mm) calculated for example coma resistant monofocal optics having semi-aspherical anterior surface profiles defined by Eq. (1) (designated in FIGS. 3A and 3B as "3 mm Example Optic Defined by Eq. (1)" and "4 mm Example Optic Defined by Eq. (1)"), and conventional aspherical monofocal optics having anterior surface profiles defined by Eq. (1) with aspheric coefficients $a_4$, $a_6$, and $a_8$ equal to zero (designated in FIGS. 3A and 3B as "3 mm Conventional Optic" and "4 mm Conventional Optic"). FIG. 3A shows the MTF plots when the optics are centered with respect to the optical axis of the eye, and FIG. 3B shows the MTF plots when the optics are decentered by 0.5 mm with respect to the optical axis of the eye. The MTF plots are computed based on monochromatic incident radiation having a wavelength of 550 nm. Tables 1A-1B provide parameters of the anterior surface of the example optics, according to the embodiment of the invention. The base curvatures of the anterior surfaces of the optics were selected such that the optic would provide a nominal optical power of 21 D.

TABLE 1A

Example Optics

| Central Thickness (mm) | Diameter (mm) | Index of Refraction |
|---|---|---|
| 0.6 mm | 6 mm | 1.55 |

TABLE 1B

Anterior Surface Parameters of Example Optics Having Semi-Aspheric Surface Profile

| Radius | $a_4$ Coefficient Range | $a_6$ Coefficient Range | $a_8$ Coefficient Range |
|---|---|---|---|
| 3 mm | $-9.6550 \times 10^{-4}$ mm to $-3.1286 \times 10^{-4}$ mm | $-1.4229 \times 10^{-4}$ mm to $2.3848 \times 10^{-4}$ mm | $-1.9439 \times 10^{-4}$ mm to $2.0641 \times 10^{-4}$ mm |

In FIG. 3A (where the optics are centered with respect to the optical axis of the eye), the through-focus MTF plots for 3 mm diameter pupils show that the example coma resistant monofocal optic design has identical optical performance to the conventional aspherical monofocal optic design. This is because the anterior surface of both the example coma resistant monofocal optic and the conventional aspherical monofocal optic are effectively identical and spherical in this region. For a pupil diameter of 4 mm, the MTF peak of the example coma resistant monofocal optic design is shifted in the myopic direction (i.e., negative direction, <0.25 D) relative to the position of the 3 mm pupil MTF peak, which results in a decrease in image quality relative to the conventional aspherical monofocal optic design. The aspheric components of the anterior surface of the example coma resistant monofocal optic design are responsible for this shift, but these components are necessary to prevent the MTF from decreasing as much as the conventional aspherical monofocal design when decentered from the optical axis of the eye, as shown in FIG. 3B.

In FIG. 3B (where the optics are decentered by 0.5 mm with respect to the optical axis of the eye), the MTF plots shows that the optical performance of the example coma resistant monofocal optic design is higher than the conventional aspherical monofocal optic design at the distance vision focus (0 diopters) at both pupil sizes. There is a hyperopic shift (positive direction, <0.25 D) in the focus because of the decentration of the lens, corresponding to a drop in image quality at the distance vision focus that can be seen for both lens designs at both pupil sizes in the decentered case. At a pupil diameter of 3 mm, a decentration of the lens by 0.5 mm decreases the MTF by 0.26 for the conventional aspherical monofocal optic design, whereas the MTF decrease for the example coma resistant monofocal optic design is 0.2, leaving the decentered MTF of the example coma resistant monofocal optic design to be higher than the ISO 11979-2 on-axis monofocal 3 mm MTF specification of 0.43 at 100 lp/mm. This is due to the additional anterior aspheric components outside of the 3 mm diameter inner region of the example coma resistant monofocal optic being illuminated within the aperture, leading to a smaller decrease in image quality compared to the conventional aspherical monofocal optic design.

At the large pupil size of 4 mm, in both designs, the asphere components of the posterior surface are counteracting the focus shift caused by the decentration of the lens, but the additional asphere components of the anterior surface of the example coma resistant monofocal optic are able to compensate for the decrease in image quality to maintain the MTF above 0.3, which is higher than some multifocal IOL designs at distance focus when the IOL is centered on the optical axis. By contrast, the MTF of the conventional aspherical monofocal optic drops below 0.2 when the IOL is decentered from the optical axis. Large pupil vision is more affected by the decentration of the IOL from the optical axis because the areas of the lens that would not normally be contributing to the vision at a particular pupil size are now illuminated. For the larger pupil diameter (4 mm), the asphericity in the outer region compensates for focal shifts and provides improved optical performance compared to the conventional aspheric design.

Figure 4:
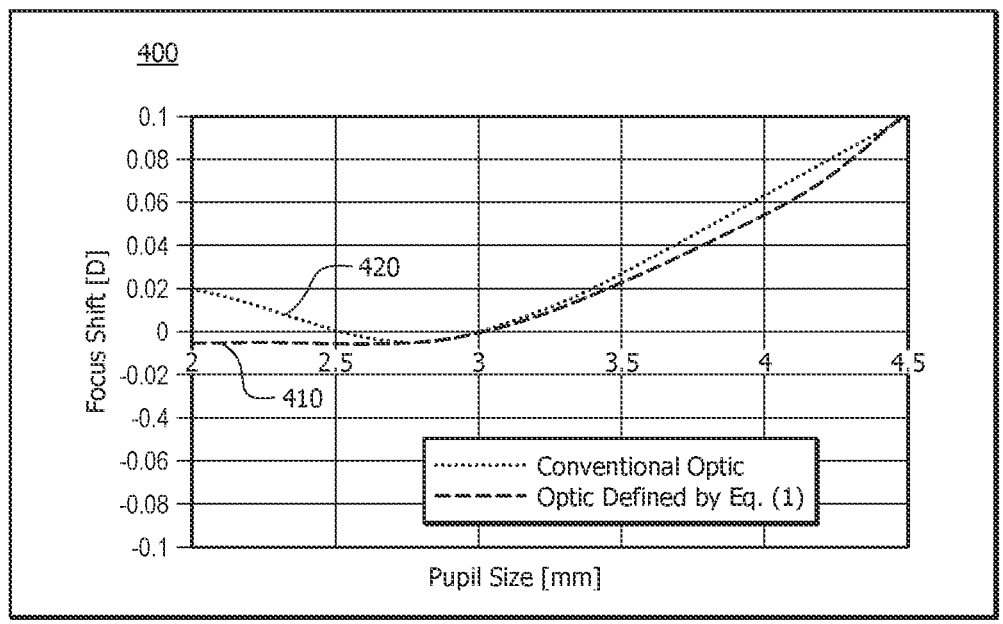
FIG. 4 illustrates a comparative plot showing focal shifts at various pupil sizes for an example optic and a conventional optic, in accordance with the present disclosure.

With reference now to FIG. 4, there is shown a plot 400 showing the focal shifts of optics 410, 420 at various pupil sizes, wherein the optics 410, 420 are centered with respect to the optical axis of the eye. According to an embodiment, the first optic 410 comprises an semi-aspherical anterior surface defined by Eq. (1) and an aspherical posterior surface. The second optic 420 comprises a conventional optic having a spherical anterior surface and an aspherical posterior surface. As illustrated in the plot 400, for pupil diameters that are less than approximately 2.4 mm, the first optic 410 minimizes focal shift (by less than −0.005 D), thereby resulting in high optical performance for small pupils. The second optic 420 generates a substantially higher focal shift (up to 0.02 D for a 2 mm pupil diameter), indicating lower performance. Thus, the presently disclosed optic design increases performance for small pupil diameters (less than 2.4 mm).

Figure 5:
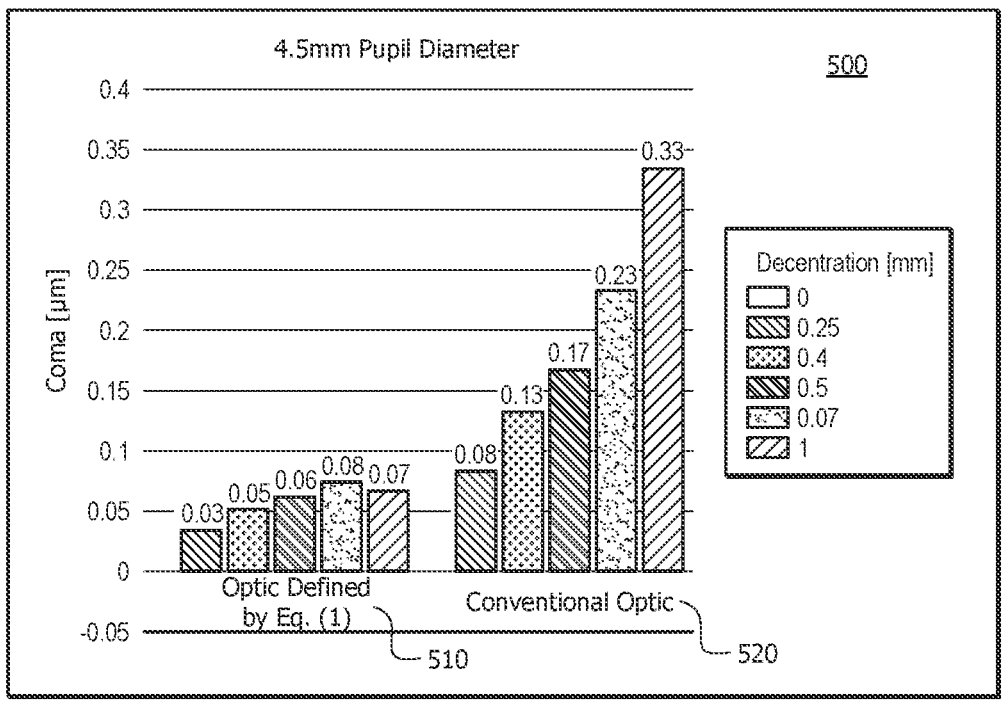
FIG. 5 illustrates a comparative graph showing coma measurements at various degrees of decentration for an example optic and a conventional optic, in accordance with the present disclosure.

Reference is now made to FIG. 5, wherein is shown a graph 500 of coma measurements for optics 510, 520 calculated at various degrees of decentration from an optical axis of an eye. The measurements compare coma results for a first optic 510 having a semi-aspherical anterior surface whose profile is defined by Eq. (1) and an aspherical posterior surface, and a second conventional optic design 520 having a spherical anterior surface and an aspherical posterior surface. Coma measurements were taken at six positions of decentration, beginning at 0 mm (no decentration) and increasing incrementally to 1 mm decentration. At 0 mm decentration, no identifiable coma was detected for either optic design. The first optic 510 displayed, at a position of 0.25 mm decentration, a coma measuring 0.03 um. As the distance of decentration was increased, the coma measurements for the first optic increased (albeit marginally) and then appeared to plateau at 0.7 mm decentration. The coma patterns for the second optic 520 were distinguishable. The second optic 520 displayed a coma measuring 0.08 um at 0.25 mm decentration. Coma measurements at each successive decentration position continued to rise in substantial increments (0.13 um coma at 0.4 mm decentration; 0.17 um coma at 0.5 mm decentration; 0.23 um coma at 0.7 decentration; and 0.33 um coma at 1.0 mm decentration). These patterns show that the presently disclosed optic more effectively reduces coma aberrations caused by decentration of the lens, as compared to conventional aspherical IOL designs.

In use, the intraocular lenses described herein are adapted to treat vision disorders and to be inserted in the human eye using conventional surgical techniques modified in accordance with the present teachings. Typically, the natural crystalline lens is first removed and the IOL can be folded into a compact size for insertion through an incision or opening in the capsular bag. Following insertion, the IOL may be manipulated to assume its proper position in the capsular bag.

A variety of techniques and materials may be employed to fabricate the lenses described in this disclosure. For example, the optic 120 of FIGS. 1A and 1B may be formed of a variety of biocompatible polymeric materials. Some suitable biocompatible materials include, without limitation, soft acrylic polymers, hydrogel, polymethymethacrylate, polysulfone, polystyrene, cellulose, acetate butyrate, or other biocompatible materials. By way of example, in an embodiment, the optic 120 may be formed of a soft acrylic polymer (cross-linked copolymer of 2-phenylethyl acrylate and 2-phenyl-ethyl methacrylate) commonly known as AcrySof®. The haptics 110 of the lenses may be formed of suitable biocompatible materials, such as those discussed above. While in some cases the optic 120 and the haptics 110 of an IOL can be fabricated as an integral unit, in other cases they can be formed separately and joined together using techniques known in the art.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

It will be appreciated that various of the above-disclosed and other features and functions, or alternatives thereof, may be desirably combined into many other different systems or applications. It will also be appreciated that various presently unforeseen or unanticipated alternative, modifications, variations, or improvements therein may be subsequently made by those skilled in the art which alternatives, variations, and improvements are also intended to be encompassed by the following claims. Those having ordinary skill in the art will appreciate that various changes can be made to the above embodiments without departing from the scope of the invention.

The invention claimed is:

1. An intraocular lens (IOL), comprising:
    an optic having an anterior surface and an opposing posterior surface disposed about an optical axis of the intraocular lens, one of the anterior and posterior surfaces having an aspherical surface profile extending from the optical axis of the intraocular lens to a radially outermost edge of the optic, the other of the anterior and posterior surfaces having a semi-aspherical surface profile comprising:
        an inner region having a substantially spherical surface profile and extending radially from the optical axis of the intraocular lens to a first boundary; and
        an outer region having an aspherical surface profile and extending radially at least beyond the first boundary to a second boundary;
    wherein the other of the anterior and posterior surfaces having the semi-aspherical surface profile is disposed to maintain a substantially diffraction-limited image quality if the intraocular lens, when inserted in a patient's eye, is centered with respect to an optical axis of the patient's eye, and balance coma aberrations if the intraocular lens, when inserted in the patient's eye, is decentered with respect to the optical axis of the patient's eye.

2. The intraocular lens of claim 1, wherein the second boundary is formed between the first boundary and the radially outermost edge of the optic.

3. The intraocular lens of claim 1, wherein the second boundary comprises the radially outermost edge of the optic.

4. The intraocular lens of claim 1, wherein a composite surface profile of the other of the anterior and posterior surfaces is defined by an equation:

$$z(x) = \frac{cx^2}{1+\sqrt{1-c^2x^2}} + a_4x^4 + a_6x^6 + a_8x^8 \text{ where } 0 < x < R,$$

wherein
- x denotes a radial distance from the optical axis of the intraocular lens,
- c denotes a base curvature of the other of the anterior and posterior surfaces,
- R denotes a total radial distance from the optical axis of the intraocular lens to the second boundary,
- $a_4$ is a fourth order aspheric coefficient,
- $a_6$ is a sixth order aspheric coefficient, and
- $a_8$ is an eighth order aspheric coefficient.

5. The intraocular lens of claim 4, wherein the $a_4$ aspheric coefficient comprises a value ranging from $-9.6550 \times 10^{-4}$ mm to $-3.1286 \times 10^{-4}$ mm.

6. The intraocular lens of claim 4, wherein the $a_6$ aspheric coefficient comprises a value ranging from $-1.4229 \times 10^{-4}$ mm to $2.3848 \times 10^{-4}$ mm.

7. The intraocular lens of claim 4, wherein the as aspheric coefficient comprises a value ranging from $-1.9439 \times 10^{-4}$ mm to $2.0641 \times 10^{-4}$ mm.

8. The intraocular lens of claim 1, wherein the inner region comprises a radius having a value ranging from 0 mm to 1.5 mm.

9. The intraocular lens of claim 1, wherein the outer region comprises a radius having a value ranging from 1.5 mm to 3.0 mm.

10. The intraocular lens of claim 1, wherein the intraocular lens is a monofocal intraocular lens.

11. The intraocular lens of claim 1, wherein the intraocular lens is one of a monofocal intraocular lens with an extended depth of focus and a multifocal intraocular lens.

12. An intraocular lens (IOL), comprising:
- an optic having an anterior surface and an opposing posterior surface disposed about an optical axis of the intraocular lens, one of the anterior and posterior surfaces having an aspherical surface profile, the other of the anterior and posterior surfaces having a semi-aspherical surface profile comprising:
  - an inner region having a substantially spherical surface profile and extending radially from the optical axis of the intraocular lens to a first boundary; and
  - an outer region having an aspherical surface profile and extending radially at least beyond the first boundary to a second boundary;

wherein the other of the anterior and posterior surfaces having the semi-aspherical surface profile is disposed to maintain a substantially diffraction-limited image quality if the intraocular lens, when inserted in a patient's eye, is centered with respect to an optical axis of the patient's eye, and balance coma aberrations if the intraocular lens, when inserted in the patient's eye, is decentered with respect to the optical axis of the patient's eye; and wherein a composite surface profile of the other of the anterior and posterior surfaces is defined by an equation:

$$z(x) = \frac{cx^2}{1+\sqrt{1-c^2x^2}} + a_4x^4 + a_6x^6 + a_8x^8 \text{ where } 0 < x < R,$$

wherein,
- x denotes a radial distance from the optical axis of the intraocular lens,
- c denotes a base curvature of the other of the anterior and posterior surfaces,
- R denotes a total radial distance from the optical axis of the intraocular lens to the second boundary,
- $a_4$ is a fourth order aspheric coefficient,
- $a_6$ is a sixth order aspheric coefficient, and
- $a_8$ is an eighth order aspheric coefficient.

13. The intraocular lens of claim 12, wherein the second boundary is formed between the first boundary and a radially outermost edge of the optic.

14. The intraocular lens of claim 12, wherein the second boundary comprises a radially outermost edge of the optic.

15. The intraocular lens of claim 12, wherein the $a_4$ aspheric coefficient comprises a value ranging from $-9.6550 \times 10^{-4}$ mm to $-3.1286 \times 10^{-4}$ mm.

16. The intraocular lens of claim 12, wherein the $a_6$ aspheric coefficient comprises a value ranging from $-1.4229 \times 10^{-4}$ mm to $2.3848 \times 10^{-4}$ mm.

17. The intraocular lens of claim 12, wherein the $a_8$ aspheric coefficient comprises a value ranging from $-1.9439 \times 10^{-4}$ mm to $2.0641 \times 10^{-4}$ mm.

18. The intraocular lens of claim 12, wherein the inner region comprises a radius having a value ranging from 0 mm to 1.5 mm.

19. The intraocular lens of claim 12, wherein the outer region comprises a radius having a value ranging from 1.5 mm to 3.0 mm.

20. The intraocular lens of claim 12, wherein the intraocular lens is a monofocal intraocular lens.

21. The intraocular lens of claim 12, wherein the intraocular lens is one of a monofocal intraocular lens with an extended depth of focus and a multifocal intraocular lens.

* * * * *